(12) United States Patent
Tao et al.

(10) Patent No.: US 12,270,741 B2
(45) Date of Patent: Apr. 8, 2025

(54) METHODS FOR AFFINITY-BASED NON-ANTIBODY CAPTURE AND PURIFICATION OF EXTRACELLULAR VESICLES

(71) Applicant: Tymora Analytical Operations, LLC, West Lafayette, IN (US)

(72) Inventors: Weiguo A. Tao, West Lafayette, IN (US); Anton Ilyuk, West Lafayette, IN (US)

(73) Assignee: Tymora Analytical Operations, LLC, West Lafayette, IN (US)

( * ) Notice: Subject to any disclaimer, the term of this patent is extended or adjusted under 35 U.S.C. 154(b) by 1122 days.

(21) Appl. No.: 16/374,713

(22) Filed: Apr. 3, 2019

(65) Prior Publication Data
US 2019/0301985 A1  Oct. 3, 2019

Related U.S. Application Data

(60) Provisional application No. 62/652,293, filed on Apr. 3, 2018.

(51) Int. Cl.
*G01N 1/40* (2006.01)
*G01N 33/53* (2006.01)
*G01N 33/543* (2006.01)

(52) U.S. Cl.
CPC ............ *G01N 1/405* (2013.01); *G01N 33/53* (2013.01); *G01N 33/54306* (2013.01); *G01N 2405/00* (2013.01)

(58) Field of Classification Search
CPC .. G01N 1/405; G01N 33/53; G01N 33/54306; G01N 2405/00; G01N 1/34; C07K 1/22; B01D 15/3804
USPC ......................................................... 530/413
See application file for complete search history.

(56) References Cited

U.S. PATENT DOCUMENTS

| | | | | |
|---|---|---|---|---|
| 8,859,252 B1* | 10/2014 | Mitschelen | .............. | C12N 9/16 435/69.1 |
| 2008/0086211 A1* | 4/2008 | Rolla | ...................... | A61L 27/32 623/16.11 |
| 2014/0322820 A1* | 10/2014 | Tao | .......................... | C07K 1/14 530/344 |
| 2015/0080248 A1* | 3/2015 | Tao | .................... | G01N 33/6848 506/18 |
| 2017/0001197 A1* | 1/2017 | He | .................... | G01N 33/57488 |
| 2017/0304787 A1* | 10/2017 | Hanada | ................... | B01F 23/45 |

OTHER PUBLICATIONS

Wan et al. ("Rapid magnetic isolation of extracellular vesicles via lipid-based nanoprobes." Nature biomedical engineering vol. 1 (2017): 0058). (Year: 2017).*

(Continued)

*Primary Examiner* — Christopher L Chin
(74) *Attorney, Agent, or Firm* — Gutwein Law; Tyler B. Droste

(57) ABSTRACT

A method is disclosed to capture and purify extracellular vesicles from biofluids via lipid affinity-based capture. The EVTRAP (Extracellular Vesicles Total Recovery And Purification) method enables capture of EVs onto modified beads. The EVTRAP method results in fast and reproducible capture and isolation of EVs with greater than 90% recovery yields.

20 Claims, 19 Drawing Sheets

(56) References Cited

OTHER PUBLICATIONS

Enderle, Daniel et al. "Characterization of RNA from Exosomes and Other Extracellular Vesicles Isolated by a Novel Spin Column-Based Method." PloS one vol. 10,8 e0136133. Aug. 28, 2015, (Year: 2015).*
Kuhn et al. (A facile protocol for the immobilisation of vesicles, virus particles, bacteria, and yeast cells. Integr Biol (Camb). Dec. 2012;4(12):1550-5). (Year: 2012).*
(51) Wang, T.; Anderson, K. W.; Turko, I. V. Anal Chem 2017, 89, 11070-11075.
(52) Filip, S.; Vougas, K.; Zoidakis, J.; Latosinska, A.; Mullen, W.; Spasovski, G.; Mischak, H.; Vlahou, A.; Jankowski, J. PLoS One 2015, 10, e0133773.
(1) Harel, M.; Oren-Giladi, P.; Kaidar-Person, O.; Shaked, Y.; Geiger, T. Mol Cell Proteomics 2015, 14, 1127-1136.
(2) Cocucci, E.; Meldolesi, J. Trends in cell biology 2015, 25, 364-372.
(3) Milane, L.; Singh, A.; Mattheolabakis, G.; Suresh, M.; Amiji, M. M. J Control Release 2015.
(4) Vader, P.; Breakefield, X. O.; Wood, M. J. Trends Mol Med 2014, 20, 385-393.
(5) Lee, T. H.; D'Asti, E .; Magnus, N.; Al-Nedawi, K.; Meehan, B.; Rak, J. Semin Immunopathol 2011, 33, 455-467.
(6) Lin, J.; Li, J.; Huang, B.; Liu, J.; Chen, X.; Chen, X. M.; Xu, Y. M.; Huang, L. F.; Wang, X. Z.
(7) Xu, R.; Greening, D. W.; Zhu, H. J.; Takahashi, N.; Simpson, R. J. The Journal of clinical investigation 2016, 126, 1152-1162.
(8) Melo, S. A.; Luecke, L. B.; Kahlert, C.; Fernandez, A. F.; Gammon, S. T.; Kaye, J.; LeBleu, V. S.; Mittendorf, E. A.; Weitz, J.; Rahbari, N.; Reissfelder, C.; Pilarsky, C.; Fraga, M. F.; Piwnica-Worms, D.; Kalluri, R. Nature 2015, 523, 177-182.
(9) Ridder, K.; Sevko, A.; Heide, J.; Dams, M.; Rupp, A. K.; Macas, J.; Starmann, J.; Tjwa, M.; Plate, K. H.; Sultmann, H.; Altevogt, P.; Umansky, V.; Momma, S. Oncoimmunology 2015, 4, e1008371.
(10) Dobrowolski, R.; De Robertis, E. M. Nat Rev Mol Cell Biol 2012, 13, 53-60.
(11) Costa-Silva, B.; Aiello, N. M.; Ocean, A. J.; Singh, S.; Zhang, H.; Thakur, B. K.; Becker, A.; Hoshino, A.; Mark, M. T.; Molina, H.; Xiang, J.; Zhang, T.; Theilen, T. M.; Garcia-Santos, G.; Williams, C.; Ararso, Y.; Huang, Y.; Rodrigues, G.; Shen, T. L.; Labori, K. J., et al. Nature cell biology 2015, 17, 816-826.
(12) An, T.; Qin, S.; Xu, Y.; Tang, Y.; Huang, Y.; Situ, B.; Inal, J. M.; Zheng, L. Journal of extracellular vesicles 2015, 4, 27522.
(13) Lobb, R. J.; Lima, L. G.; Moller, A. Seminars in cell & developmental biology 2017.
(14) Sanchez, C. A.; Andahur, E. I.; Valenzuela, R.; Castellon, E. A.; Fulla, J. A.; Ramos, C. G.; Trivino, J. C. Oncotarget 2016, 7, 3993-4008.
(15) Hoshino, A.; Costa-Silva, B.; Shen, T. L.; Rodrigues, G.; Hashimoto, A.; Tesic Mark, M.; Molina, H.; Kohsaka, S.; Di Giannatale, A.; Ceder, S.; Singh, S.; Williams, C.; Soplop, N.; Uryu, K.; Pharmer, L.; King, T.; Bojmar, L.; Davies, A. E.; Ararso, Y.; Zhang, T., et al. Nature 2015, 527, 329-335.
(16) Verma, M.; Lam, T. K.; Hebert, E.; Divi, R. L. BMC Clin Pathol 2015, 15, 6.
(17) Yang, K. S.; Im, H.; Hong, S.; Pergolini, I.; Del Castillo, A. F.; Wang, R.; Clardy, S.; Huang, C. H.; Pille, C.; Ferrone, S.; Yang, R.; Castro, C. M.; Lee, H.; Del Castillo, C. F.; Weissleder, R. Sci Transl Med 2017, 9.
(18) Sokolova, V.; Ludwig, A. K.; Hornung, S.; Rotan, O.; Horn, P. A.; Epple, M.; Giebel, B. Colloids and surfaces. B, Biointerfaces 2011, 87, 146-150.
(19) Boukouris, S.; Mathivanan, S. Proteomics Clin Appl 2015, 9, 358-367.
(20) Van der Mijn, J. C.; Sol, N.; Mellema, W.; Jimenez, C. R.; Piersma, S. R.; Dekker, H.; Schutte, L. M.; Smit, E. F.; Broxterman, H. J.; Skog, J.; Tannous, B. A.; Wurdinger, T.; Verheul, H. M. Journal of extracellular vesicles 2014, 3, 25657.
(21) Lotvall, J.; Hill, A. F.; Hochberg, F.; Buzas, E. I.; Di Vizio, D.; Gardiner, C.; Gho, Y. S.; Kurochkin, I. V.; Mathivanan, S.; Quesenberry, P.; Sahoo, S.; Tahara, H.; Wauben, M. H.; Witwer, K. W.; Thery, C. Journal of extracellular vesicles 2014, 3, 26913.
(22) Witwer, K. W.; Buzas, E. I.; Bemis, L. T.; Bora, A.; Lasser, C.; Lotvall, J.; Nolte-'t Hoen, E. N.; Piper, M. G.; Sivaraman, S.; Skog, J.; Thery, C.; Wauben, M. H.; Hochberg, F. Journal of extracellular vesicles 2013, 2.
(23) Taylor, D. D.; Shah, S. Methods 2015, 87, 3-10.
(24) Nakai, W.; Yoshida, T.; Diez, D.; Miyatake, Y.; Nishibu, T.; Imawaka, N.; Naruse, K.; Sadamura, Y.; Hanayama, R. Sci Rep 2016, 6, 33935.
(25) Lamparski, H. G.; Metha-Damani, A.; Yao, J. Y.; Patel, S.; Hsu, D. H.; Ruegg, C.; Le Pecq, J. B. Journal of immunological methods 2002, 270, 211-226.
(26) Stranska, R.; Gysbrechts, L.; Wouters, J.; Vermeersch, P.; Bloch, K.; Dierickx, D.; Andrei, G.; Snoeck, R. J Transl Med 2018, 16, 1.
(27) Zeringer, E.; Li, M.; Barta, T.; Schageman, J.; Pedersen, K. W.; Neurauter, A.; Magdaleno, S.; Setterquist, R.; Vlassov, A. V. World J Methodol 2013, 3, 11-18.
(28) Niu, Z.; Pang, R. T. K.; Liu, W.; Li, Q.; Cheng, R.; Yeung, W. S. B. PLoS One 2017, 12, e0186534.
(29) Mathivanan, S.; Lim, J. W.; Tauro, B. J.; Ji, H.; Moritz, R. L.; Simpson, R. J. Mol Cell Proteomics 2010, 9, 197-208.
(30) Yoo, C. E.; Kim, G.; Kim, M.; Park, D.; Kang, H. J.; Lee, M.; Huh, N. Anal Biochem 2012, 431, 96-98.
(31) Enderle, D.; Spiel, A.; Coticchia, C. M.; Berghoff, E.; Mueller, R.; Schlumpberger, M.; Sprenger-Haussels, M.; Shaffer, J. M.; Lader, E.; Skog, J.; Noerholm, M. PLoS One 2015, 10, e0136133.
(32) Welton, J. L.; Webber, J. P.; Botos, L. A.; Jones, M.; Clayton, A. Journal of extracellular vesicles 2015, 4, 27269.
(33) Van Deun, J.; Mestdagh, P.; Sormunen, R.; Cocquyt, V.; Vermaelen, K.; Vandesompele, J.; Bracke, M.; De Wever, O.; Hendrix, A. Journal of extracellular vesicles 2014, 3.
(34) Taylor, D. D.; Zacharias, W.; Gercel-Taylor, C. Methods Mol Biol 2011, 728, 235-246.
(35) Rana, S.; Yue, S.; Stadel, D.; Zoller, M. Int J Biochem Cell Biol 2012, 44, 1574-1584.
(36) Peterson, M. F.; Otoc, N.; Sethi, J. K.; Gupta, A.; Antes, T. J. Methods 2015, 87, 31-45.
(37) Gholizadeh, S.; Shehata Draz, M.; Zarghooni, M.; Sanati-Nezhad, A.; Ghavami, S.; Shafiee, H.; Akbari, M. Biosens Bioelectron 2017, 91, 588-605.
(38) Tang, Y. T.; Huang, Y. Y.; Zheng, L.; Qin, S. H.; Xu, X. P.; An, T. X.; Xu, Y.; Wu, Y. S.; Hu, X. M.; Ping, B. H.; Wang, Q. Int J Mol Med 2017, 40, 834-844.
(39) Bijnsdorp, I. V.; Maxouri, O.; Kardar, A.; Schelfhorst, T.; Piersma, S. R.; Pham, T. V.; Vis, A.; van Moorselaar, R. J.; Jimenez, C. R. Journal of extracellular vesicles 2017, 6, 1313091.
(40) Royo, F.; Zuniga-Garcia, P.; Sanchez-Mosquera, P.; Egia, A.; Perez, A.; Loizaga, A.; Arceo, R.; Lacasa, I.; Rabade, A.; Arrieta, E.; Bilbao, R.; Unda, M.; Carracedo, A.; Falcon-Perez, J. M. Journal of extracellular vesicles 2016, 5, 29497.
(41) Liang, L. G.; Sheng, Y. F.; Zhou, S.; Inci, F.; Li, L.; Demirci, U.; Wang, S. Methods Mol Biol 2017, 1660, 355-364.
(42) Chen, I. H.; Xue, L.; Hsu, C. C.; Paez, J. S.; Pan, L.; Andaluz, H.; Wendt, M. K.; Iliuk, A. B.; Zhu, J. K.; Tao, W. A. Proc Natl Acad Sci U S A 2017, 114, 3175-3180.
(43) Cvjetkovic, A.; Lotvall, J.; Lasser, C. Journal of extracellular vesicles 2014, 3.
(44) Simak, J.; Gelderman, M. P. Transfus Med Rev 2006, 20, 1-26.
(45) Horstman, L. L.; Jy, W.; Jimenez, J. J.; Ahn, Y. S. Front Biosci 2004, 9, 1118-1135.
(46) Voloshin, T.; Fremder, E.; Shaked, Y. Cancer Microenviron 2014, 7, 11-21.
(47) Kowal, J.; Arras, G.; Colombo, M.; Jouve, M.; Morath, J. P.; Primdal-Bengtson, B.; Dingli, F.; Loew, D.; Tkach, M.; Thery, C. Proc Natl Acad Sci U S A 2016, 113, E968-977.
(48) Keerthikumar, S.; Chisanga, D.; Ariyaratne, D.; Al Saffar, H.; Anand, S.; Zhao, K.; Samuel, M.; Pathan, M.; Jois, M.; Chilamkurti, N.; Gangoda, L.; Mathivanan, S. J Mol Biol 2016, 428, 688-692.

(56) References Cited

OTHER PUBLICATIONS

(49) Mathivanan, S.; Fahner, C. J.; Reid, G. E.; Simpson, R. J. Nucleic Acids Res 2012, 40, D1241-1244.
(50) Simpson, R. J.; Kalra, H.; Mathivanan, S. Journal of extracellular vesicles 2012, 1.

* cited by examiner

B.

| | EV2/EV1 | EV3/EV1 | EV4/EV1 |
|---|---|---|---|
| Exosome markers combined signal increase over EV1 (UC) | 4.4x | 8.8x | 16.9x |
| Free urine proteins combined signal increase over EV1 (UC) | 4.9x | 9.3x | 16.5x |

Figure 4B

METHODS FOR AFFINITY-BASED NON-ANTIBODY CAPTURE AND PURIFICATION OF EXTRACELLULAR VESICLES

CROSS REFERENCE

This application is a U.S. non-provisional patent application of and claims the priority of U.S. provisional patent application, Ser. No. 62/652,293 filed on Apr. 3, 2018, and incorporates by reference the subject matter thereof in its entirety.

FIELD

A method is disclosed to capture and purify extracellular vesicles from biofluids via lipid affinity-based capture.

BACKGROUND

Currently the most widespread method for clinical cancer profiling and disease diagnosis involves a tumor biopsy, an invasive and painful procedure, and one that certainly is impractical for early-stage detection. As cancer becomes a more chronic disease that requires active monitoring over longer periods of time, tissue biopsies on a continuous basis are no longer a realistic scenario. As a result, "liquid biopsies"—analysis of biofluids such as plasma, serum, urine—have gained much attention as a potentially useful source of diagnostic biomarkers. The biofluid may be plasma, serum, urine, saliva, sputum, cell culture media, amniotic fluid, interstitial fluid, sweat, tears, or cerebral spinal fluid. Liquid biopsies offer numerous advantages for a clinical analysis, including non-invasive collection, a suitable sample source for longitudinal disease monitoring, better screenshot of tumor heterogeneity, higher stability and sample volumes, faster processing times, lower rejection rates and cost. However, the most common focus of liquid biopsy—CTCs and ctDNA—have not lived up to the high expectations due to their heterogeneity, extreme rarity and fragmentation levels.

To help overcome these challenges a new field has generated a lot of interest over the past few years—profiling of cell-secreted extracellular vesicles (EVs). EVs generally include smaller size exosomes derived from multivesicular endosome-based secretions, and microvesicles (MVs) derived from the plasma membrane. The EVs provide an effective and ubiquitous method for intercellular communication, stimulation of immune system, removal of harmful materials and many more functions. As EVs are shed into virtually every biological fluid and embody a good representation of their parent cell, analysis of the EV cargo has great potential for biomarker discovery and disease diagnosis. Interestingly, researchers have also found many differentiating characteristics of the cancer cell-derived cargo, including driver mutations, molecular subtypes, active miRNA and proteins, which possess metastatic properties and have been shown to prepare the pre-metastatic niche. Particularly promising are the findings that these EV-based disease markers can be identified well before the onset of symptoms or physiological detection of a tumor, making them promising candidates for early-stage cancer and other disease detection. In addition, EVs are membrane-covered nanoparticles, which protects the inside contents from external proteases, phosphatases and other enzymes.

Given the immaturity of EV analysis, a standardized method for collecting and processing EVs has not yet been developed. Differential centrifugation with ultracentrifugation (UC) as the final step is generally considered the "gold standard" for EV isolation (particularly for exosome purification). Here, the vesicles are pelleted down after centrifugation of a biological fluid at a high g-force (typically 100K×g). However, this approach is very time-consuming (typically 6-22 hours), requires expensive equipment, is low-throughput and overall not suitable for a clinical setting due to poor reproducibility. In addition, multiple studies have shown that the exosome recovery rate after ultracentrifugation is only 5-25%. Several other groups have published and commercialized new methods for EV isolation, which include polymer-induced precipitation, antibody-based affinity capture of outer membrane proteins, affinity filtration, size-exclusion chromatography, etc. However, each one has its own limitations. For example, polymer-based precipitation, such as PEG, typically results in low specificity and a large number of high-abundant contaminating non-EV proteins being extracted as well. This issue may not be a major concern for RNA/DNA analysis, but it makes it unusable for proteome or phosphoproteome explorations. Additionally, the precipitating polymer is not fully compatible with subsequent MS analysis. Affinity-based exosome capture approach does offer improved specificity, but is constrained to small volumes, results in very low overall recovery yield and can be significantly limited by tumor heterogeneity and target antigen changes over time.

Majority of the new methods that have been developed so far aim at reducing the time and cost associated with ultracentrifugation. Many have certainly succeeded in this goal. They also typically have higher reproducibility and demonstrate exosome recovery rates that are usually similar or slightly worse than ultracentrifugation. These can certainly be judged as a significant improvement over UC and can be used as good fast alternatives for EV isolation. However, at 5-25% published yields, the efficiency of isolation still leaves much room for improvement.

SUMMARY

Here, we present a novel method for fast and reproducible capture and isolation of EVs with >90% recovery yields. The approach, herein tentatively named EVTRAP (Extracellular Vesicles Total Recovery And Purification), enables complete capture of EVs onto beads modified with a combination of hydrophilic and aromatic lipophilic groups that we found to have a unique affinity toward lipid-coated EVs. We have developed both magnetic and non-magnetic versions of the beads and used them to demonstrate unprecedented isolation efficiency through EV marker detection and proteomic experiments (workflow illustration for the magnetic version shown in FIG. 1). Using the EVTRAP capture and our improved protein extraction method, we were routinely able to detect >16,000 unique peptides from ~2,000 unique proteins in a single 90 min LC-MS run from only 200 μL urine. We also compared this method to standard EV isolation techniques from urine, saliva and plasma. We found that all detected markers and exosome-enriched proteins were captured at significantly higher levels by EVTRAP. Finally, we have also demonstrated the ability to detect EV markers directly on beads after EVTRAP capture in a quantitative manner.

BRIEF DESCRIPTION OF THE DRAWINGS

The above-mentioned and other features of this disclosure, and the manner of attaining them, will become more apparent and the disclosure itself will be better understood by reference to the following description of embodiments of the disclosure taken in conjunction with the accompanying drawings, wherein:

FIG. 4B displays the fold increase in total proteome intensity of known exosomal proteins and free urine proteins from LC-MS data compared to UC sample (EV1=100K UC pellet; EV2=EVTRAP of 100K UC supernatant; EV3=EVTRAP of 10K supernatant; EV4=EVTRAP of urine).

Figure 1:
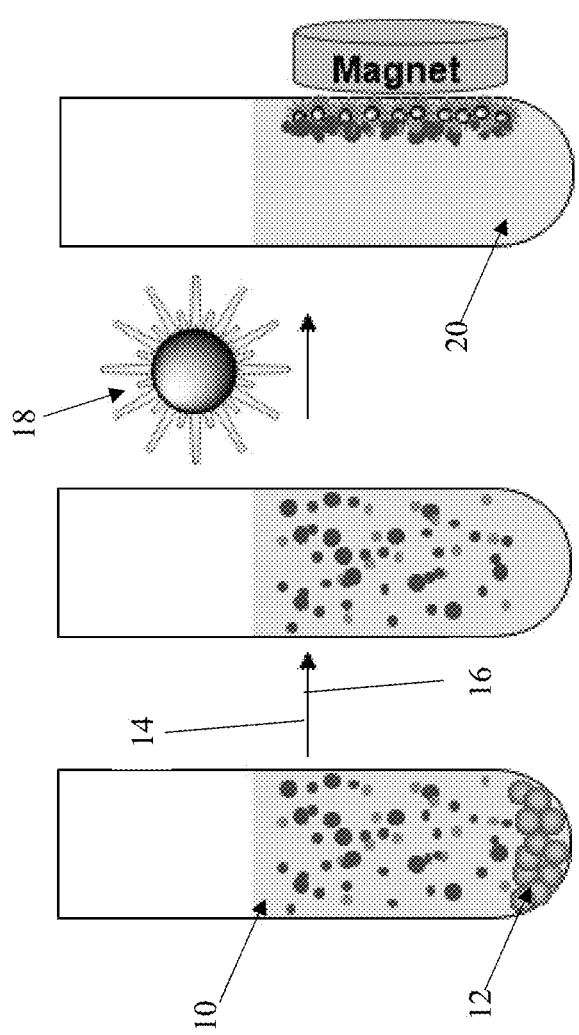
FIG. 1 illustrates the workflow of EV capture by magnetic EVTRAP.

Corresponding reference characters indicate corresponding parts throughout the several views. Although the drawings represent embodiments of the present disclosure, the drawings are not necessarily to scale and certain features may be exaggerated in order to better illustrate and explain the present disclosure.

DETAILED DESCRIPTION OF THE EXEMPLARY EMBODIMENTS

The embodiments disclosed below are not intended to be exhaustive or limit the disclosure to the precise forms disclosed in the following detailed description. Rather, the embodiments are chosen and described so that others skilled in the art may utilize their teachings.

The method is based on silica beads, agarose beads, magnetic beads and/or other solid-phase platform. The beads/platform are coated/modified with a combination of a hydrophilic group (e.g. polyethylene oxide, polyethylene glycol, etc.) and an aromatic hydrocarbon lipophilic or hydrophobic group (e.g. phenyl ether, phenyl ethoxylate, octyl phenyl ethoxylate, their variations or the like). These coatings may include ionic or non-ionic surfactants. Such a combination in various proportions has an affinity to lipid-covered extracellular vesicles without substantial binding to free proteins or other molecules in the sample. Thus, lipid-coated EVs can specifically bind to such combinations of affinity groups.

An additional group can be added which includes dendrimer-based foundation that can be linked between the affinity groups and the beads to increase the surface area. The dendrimer can be also modified with titanium, zirconium, iron, zinc or similar ions to improve binding of phospholipids that coat extracellular vesicles.

Various compounds may be added to the samples, including but not limited to detergents, salts, buffers, surfactants and others to improve EV capture efficiency and/or prevent binding of the free proteins in the sample.

Following the capture of the EVs onto the affinity beads, the internal or membranous EV contents can be extracted by a surfactant-based solution, triethylamine elution, on-beads digestion, high temperature elution, electric pulse-based extraction or similar. Other extraction solutions may include urea, thiourea, SDS, Triton, deoxycholate or any other molecules and conditions capable of disrupting EV membrane or eluting intact EVs off the affinity beads/platform.

The extracted/isolated EV cargo may include proteins, post-translationally modified proteins, DNA, mRNA, miRNA, metabolites, gene mutations or the like.

After EV capture, the surface markers can also be detected directly on the beads without the need for extraction or elution. The detection can be carried out using antibodies, aptamers, incorporated labels, etc.

The method can also be used to quantify and characterize EVs themselves, rather than their cargo.

Cells and large apoptotic bodies should be removed with low-speed centrifugation to prevent binding to the affinity beads/platform.

The extracted/bound EVs and their contents can be used for research, biomarker discovery and/or diagnostic purposes, where the presence/absence or increased/decreased levels of certain EVs or their cargo molecules can serve as an indication of a disease state.

After capture and extraction, the internal EV cargo may be analyzed and/or detected by a variety of methods, including ELISA, microarrays, Western Blot, mass spectrometry, PCR, RT-PCR, NGS, spectroscopy, NTA, DLS, binding probes, and many others.

Results
Validation and Comparison of EVTRAP Capture Efficiency

Total EV and/or exosome capture and purification has been the focus of many recent studies, with particular consideration toward simple and easy protocol. The goal of replacing ultracentrifugation (UC) as the method of choice is an important one, although not yet achieved due to significant limitations of other proposed technologies. Here, we present a novel beads-based capture method for effective EV isolation, termed EVTRAP (Extracellular Vesicles Total Recovery And Purification). It enables the capture of complete EV profile based on the lipid bilayer structure of these vesicles and the unique combination of the hydrophilic and aromatic lipophilic groups on the synthesized beads. Either a complete EV population can be captured, or only exosomes when the microvesicles are removed through 10K×g centrifugation (as a preparative step for UC method as well).

Example 1

A urine sample is analyzed via two different methods to capture and purify extracellular vesicles, ultracentrifugation and EVTRAP.

For the initial comparison and method validation, we used 500 µL urine 10 and removed cells 12 and apoptotic bodies 12 through low speed centrifugation 14. We then filtered and concentrated urine using a 100 kDa filtration step 16. This allows for the sample volumes to be more manageable through 10× concentration. But more importantly, step 16 removes the majority of the free proteins and small molecules while leaving EV population intact.

Thus, we were able to run a portion of the filtered sample directly on a gel to serve as the direct control of the complete EV population. After the ultracentrifugation step (100K UC), the pellet was used directly or washed with PBS once or twice and centrifuged again. Then a pellet portion corresponding to 50 µL concentrated urine (500 µL original urine) was loaded on the gel after protein extraction by boiling with LDS loading buffer. The supernatant from 100K UC step was dried and loaded on the gel in the same proportion (equivalent to 50 µL concentrated urine).

Figure 2A:
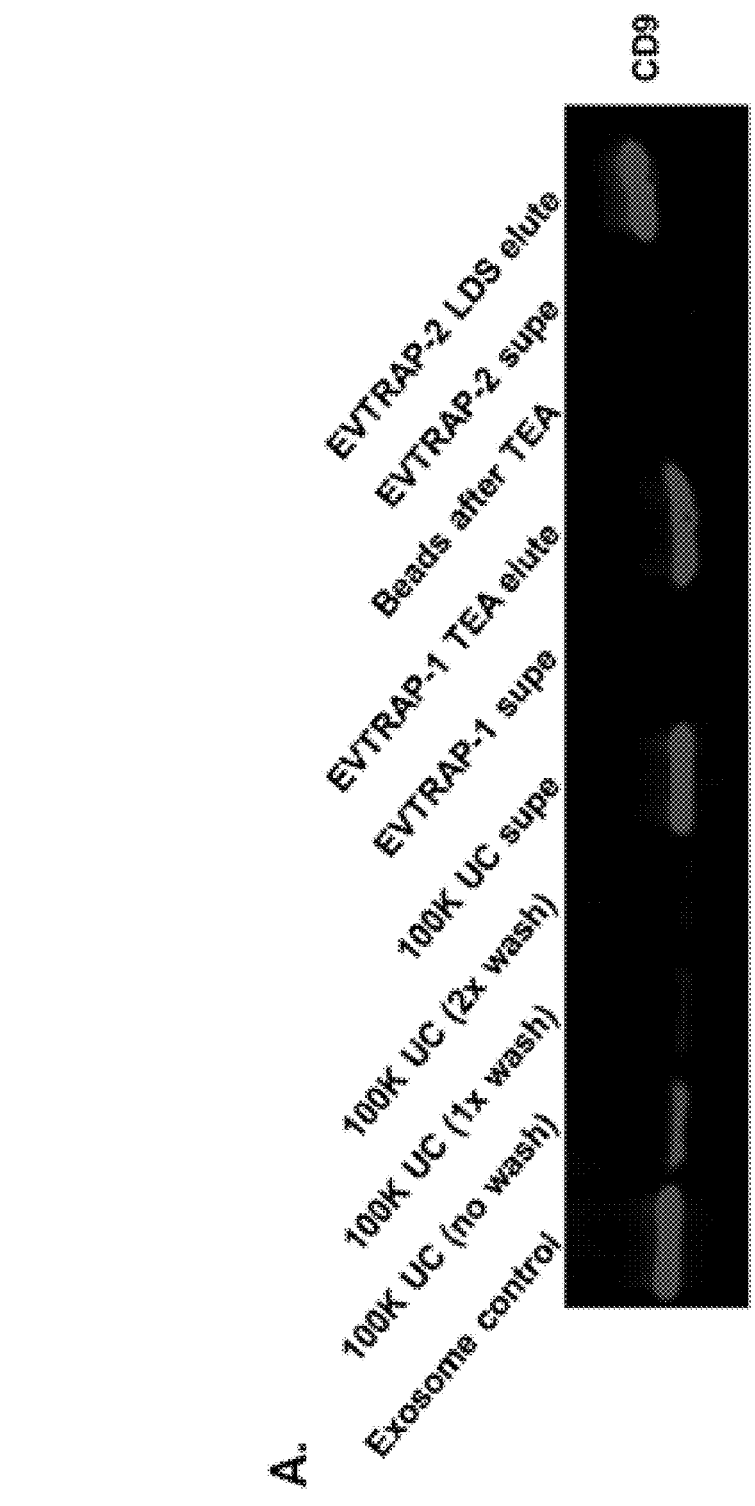
FIG. 2A displays the urine comparison between Ultracentrifugation (UC) and EVTRAP for exosome capture via detection of CD9 exosome marker using Western Blot.

50 µL concentrated urine from step 16 was also captured by the EVTRAP method 18 of FIG. 1. After 1-hour incubation, the supernatant 20 (unbound fraction; described as "EVTRAP-1 supe" in FIGS. 2A and 2B) was collected, dried and loaded on the gel as illustrated in FIG. 2A.

Figure 2B:
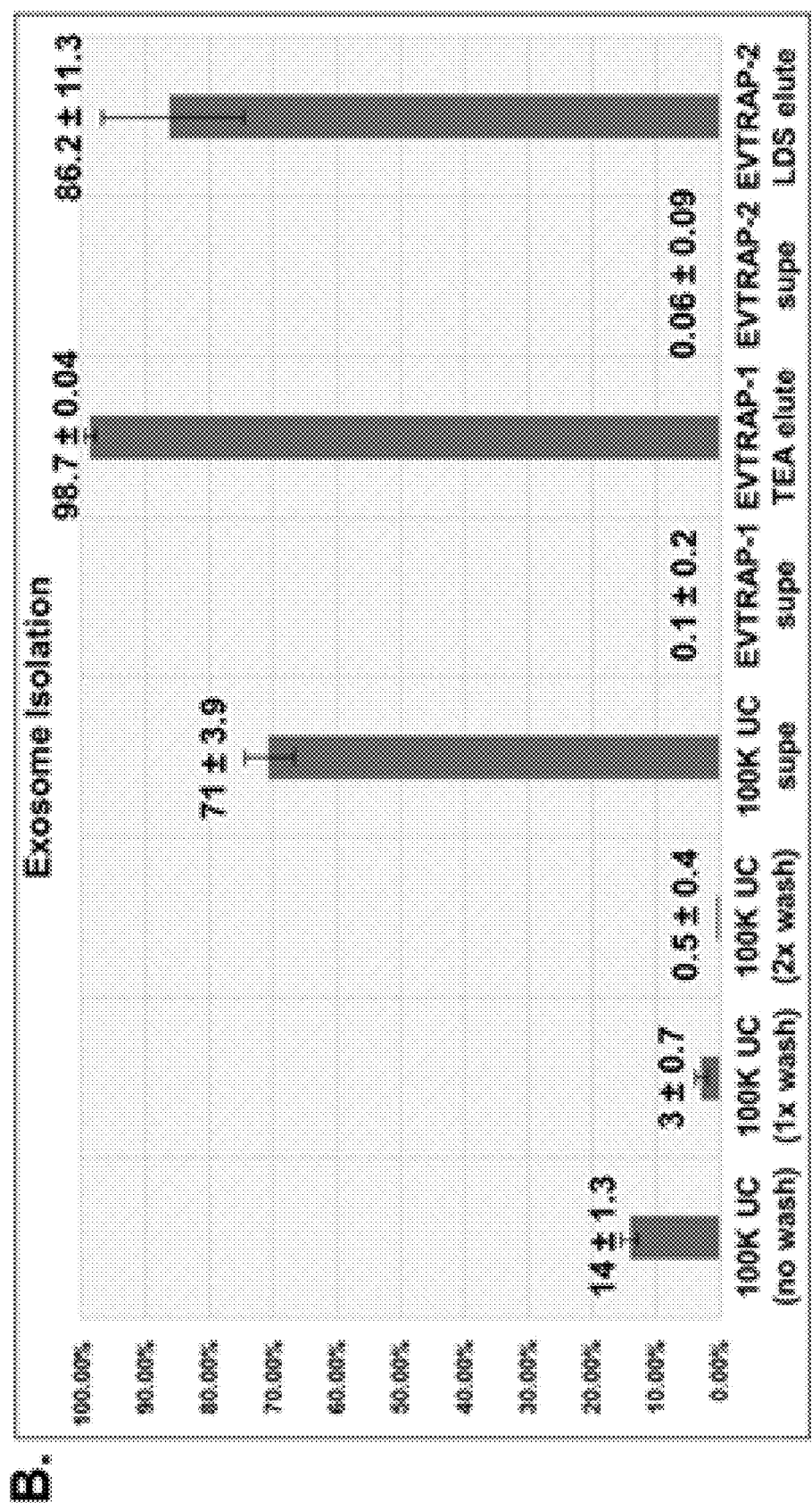
FIG. 2B displays the urine comparison between UC and EVTRAP for exosome capture via quantitation of WB data in FIG. 2A as a percent recovery from the control sample (exosome control=100%). Each point represents average and standard deviation of a minimum 5 separate experiments on the same or different blots.
Figure 2C:
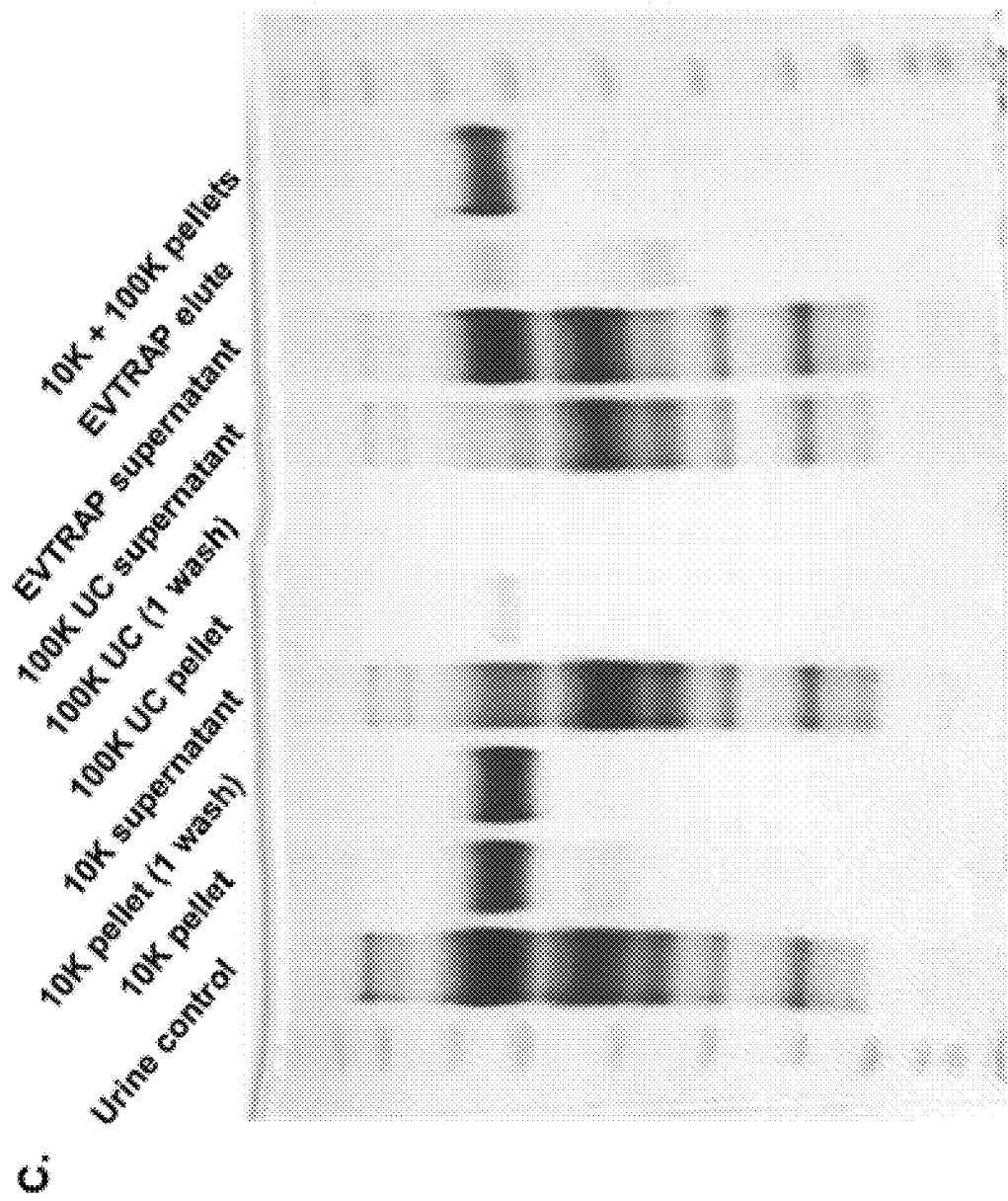
FIG. 2C displays the urine comparison between UC and EVTRAP for exosome capture via silver stain total protein detection of global EV population capture from direct unfiltered urine.
Figure 2D:
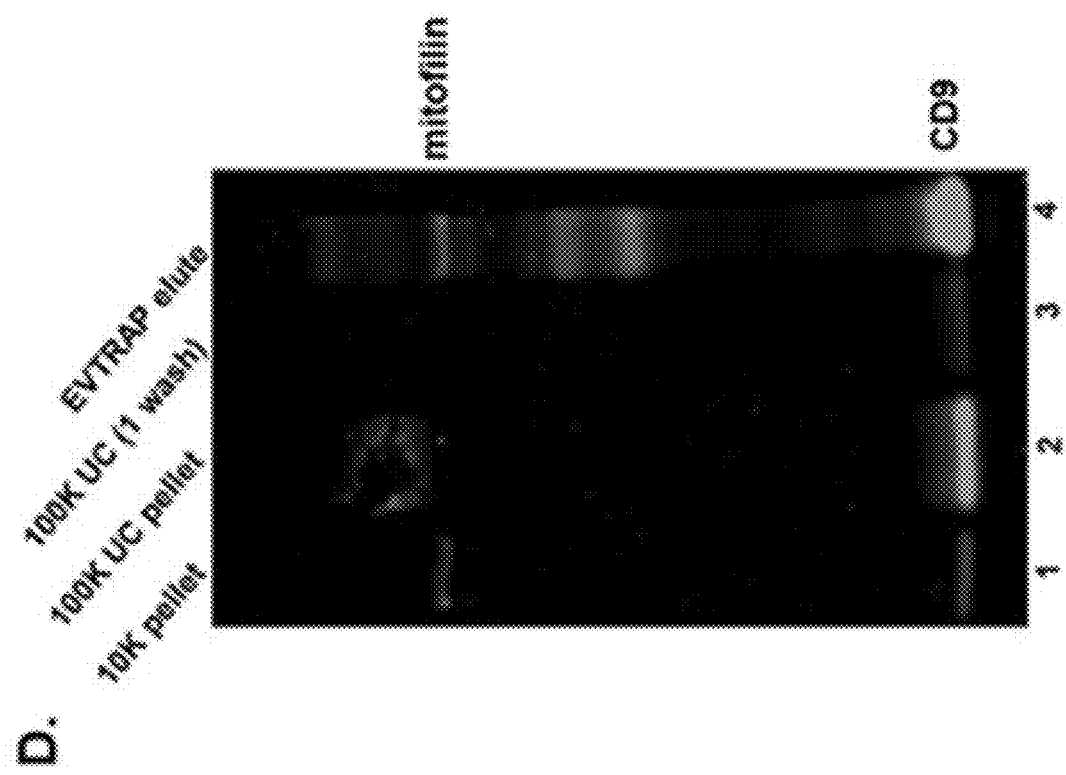
FIG. 2D displays the urine comparison between UC and EVTRAP for exosome capture via detection of CD9 (exosome marker) and mitofilin (MV marker) using Western Blot from unfiltered urine. Lane 1 contains 10K UC pellet, lane 2 contains 100K UC pellet, lane 3 contains 100K UC supernatant after one wash, and lane 4 contains the elute from EVTRAP.

In two variations of the EVTRAP experiment (described as "EVTRAP-1" and "EVTRAP-2" in FIGS. 2A and 2B), the captured EVs were eluted by incubation for 10 minutes with triethylamine (TEA) or by boiling in LDS buffer directly to determine whether elution was complete. All samples were loaded on the same gel and detected by Western Blot using a primary antibody for a common exosome marker, CD9. This experiment was carried out at least 5 separate times. A representative blot is shown in FIG. 2A, and the quantitative values for each CD9 band signal are listed in the bar graph in FIG. 2B. A few other representative blots are included in FIG. 2C, 2D, 3, 5A. As the results show, ultracentrifugation step indeed captures only a portion of the exosomes—14% on average in our case (described as "100K UC (no wash)" in FIGS. 2A and 2B)—a recovery rate similar to other studies. Washing of the UC pellet, as is a commonplace procedure, further decreased the yield (described as "100K UC (1× wash)" and "100K UC (2× wash)" in FIGS. 2A and 2B). Detection of the UC supernatant (described as "100K UC supe" in FIGS. 2A and 2B) further confirmed the incomplete capture, as it is expected to see a large percentage of EVs remaining in the supernatant. In contrast, EVTRAP method resulted in no detectable CD9-containing exosomes in the supernatant (unbound fraction; described as "EVTRAP-1 supe" and "EVTRAP-2 supe" in FIGS. 2A and 2B), with vast majority of the exosomes being captured and eluted off (almost 99% for TEA elution and >86% for LDS elution compared to the original control). As shown in FIG. 2B, the recovery and reproducibility of EVTRAP are outstanding, resulting in standard deviation of 0.04% for TEA-based elution.

EVTRAP Comparison of Direct Unfiltered Urine Samples

Figure 2E:
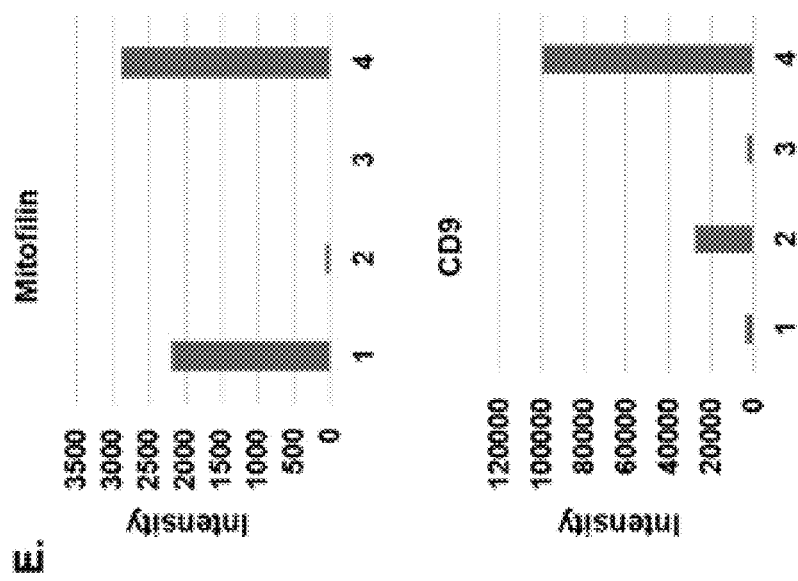
FIG. 2E displays the urine comparison between UC and EVTRAP for exosome capture via quantitation of the Western Blot signal in FIG. 2D.
Figure 3:
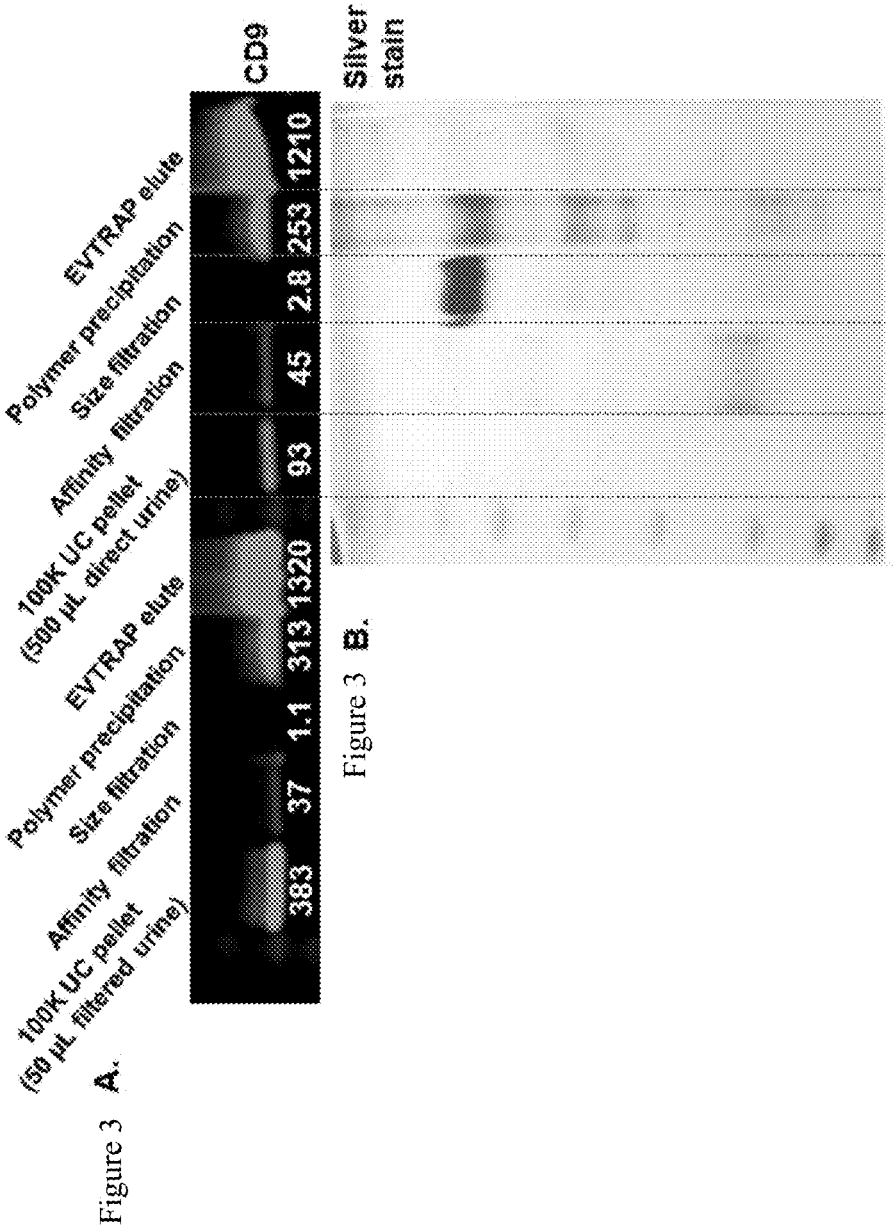
FIG. 3A displays a urine exosome capture comparison by CD9 Western Blot between ultracentrifugation (100K UC), EVTRAP and three commercial methods, with signal intensity listed under each band. The experiment was conducted twice and compared to 100K UC pellet from 10× concentrated filtered urine and 100K UC pellet from direct unfiltered urine.
FIG. 3B displays a western blot with silver stain comparison data between ultracentrifugation (100K UC), EVTRAP and three commercial methods (all lanes in the silver stain are matched to the CD9 Western Blot labels above in FIG. 3A).

In the initial experiments, it was convenient to use filtered 10× concentrated urine for comparison so that the control urine sample can be analyzed as well. Another measure of success for such a method would be the direct isolation from urine without any extensive pretreatment steps. After a short low-speed centrifugation for cells and apoptotic bodies removal, urine samples (1 mL each) were subjected to 10K×g centrifugation (10K pellet for MVs collection), 100K×g centrifugation with or without PBS wash (100K UC pellet for exosomes collection), or EVTRAP capture (for MVs+exosomes collection). It has been previously shown that microvesicles (MVs) can be as valuable for diagnostic purposes as exosomes, therefore MVs capture by EVTRAP would also be desirable. To examine the exosomes and MVs capture efficiency, we detected CD9 signal (exosome marker) and mitofilin signal (MV marker) simultaneously (See FIG. 2D; signal quantitation in FIG. 2E). As expected, since mitofilin has been reported as the marker for microvesicles (larger/medium EVs), majority of its signal was detected in the 10K pellet. Likewise, the majority of the CD9 was found in the 100K UC fraction. By comparison, EVTRAP enabled a much more complete capture of exosomes than 100K ultracentrifugation (4-fold increase; >20-fold increase if the pellet was washed once), while still allowing for the complete simultaneous capture of the MVs.

Despite EV capture analysis, another important feature is the purity of the captured EVs. To examine the amount of free protein contamination present in each sample, we used 50 µL of direct urine for each experimental treatment and detected with silver stain for total protein analysis (see FIG. 2C). As expected, 100K UC sample had very little contamination when compared to direct urine control, and even less after the PBS wash. However, when analyzing the 10K pellet, we saw a significant contamination even after the PBS wash. This result suggests the differential centrifugation does not work well for microvesicle capture due to very high volume of free protein pelleting. By comparison, EVTRAP isolation showed the vast majority of the contaminating proteins present in the unbound supernatant fraction, with very few contaminants eluting together with EVs (See "EVTRAP elute" in FIG. 2C). Compared to the complete EV capture by differential ultracentrifugation (10K pellet+ 100K pellet), EVTRAP exhibited much lower amount of contamination.

Example 2

Two different methods to capture and purify extracellular vesicles, ultracentrifugation and EVTRAP, are used to capture the exosome. Then the exosome is analyzed via western blot.

Besides ultracentrifugation and as best illustrated in FIGS. 3A and 3B, the EVTRAP method was compared to other frequently used approaches: membrane affinity spin method, size-based filtration tube, and polymer-based EV precipitation. Direct urine was used in each case and 500 µL equivalent was run after capture on two different gels and detected by anti-CD9 antibody (See FIG. 3A) or silver stain for purity assessment (See FIG. 3B). For 100K UC control, 500 µL direct urine or 50 µL filtered 10× concentrated urine was used for a more complete evaluation. As the results in FIG. 3A demonstrate, the alternative methods produced somewhat similar exosome recovery signal compared to 100K ultracentrifugation, matching the previously published results for these methods. When compared to 100K UC pellet from unfiltered urine, the polymer-based EV precipitation even produced higher exosome yield, although the contamination level was also much higher (See FIG. 3B). Nonetheless, EVTRAP still produced the highest exosome recovery yield compared to any other approach (FIG. 3A) with lower level of contamination (FIG. 3B).

Example 3

Figure 4A:
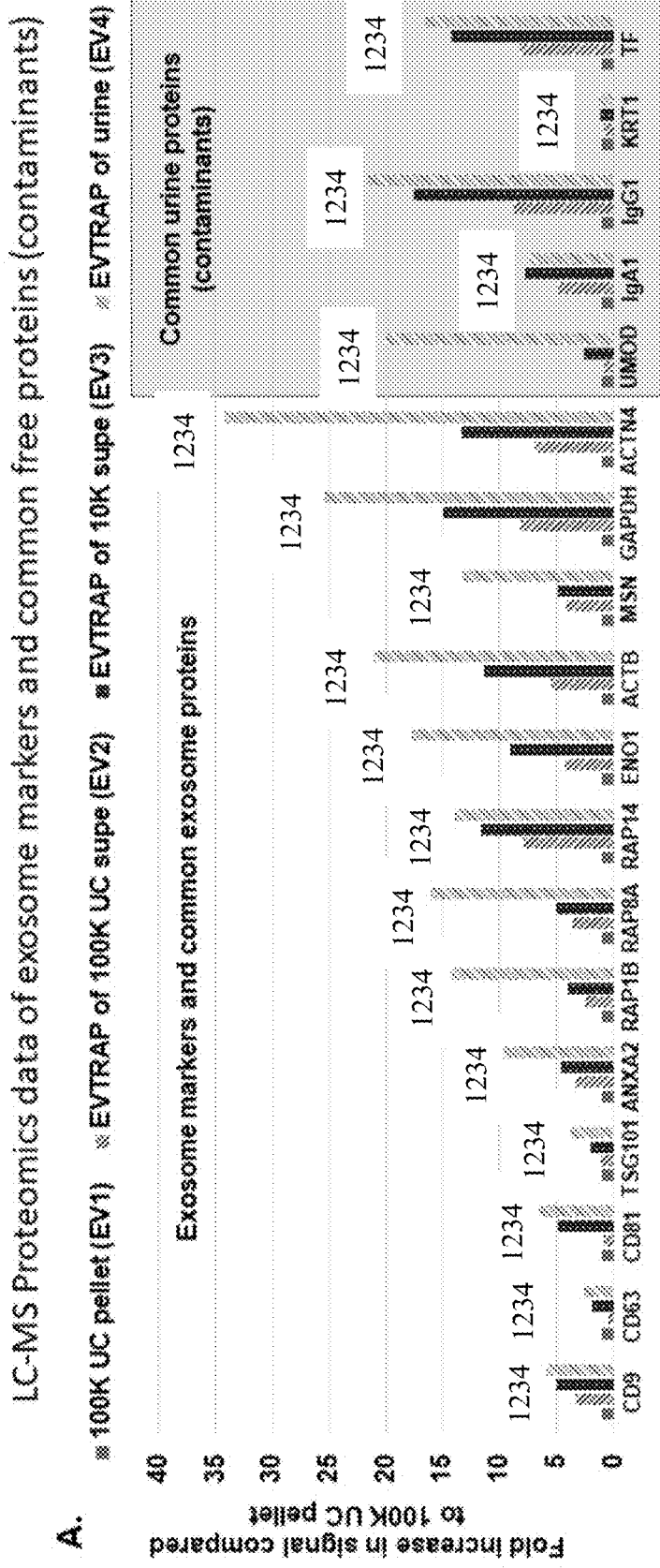
FIG. 4A displays LC-MS total proteome analysis of 100K UC and EVTRAP samples from urine via quantitation of 13 common exosome proteins and 5 free urine proteins.

As best illustrated in FIGS. 4A and 4B, two different methods to capture and purify extracellular vesicles, ultracentrifugation and EVTRAP, are used to capture the exosome. Then the exosome is analyzed via LC-MS.
Full Proteome Comparison of the Captured EVs Mass spectrometry analysis enables the detection and quantitation of hundreds or thousands of proteins in a single experiment, while uncovering previously unknown targets. For the LC-MS proteome analysis, we used 10 mL of urine for each treatment as the starting material and filtered/concentrated it down to 1 mL each. Some of the samples were centrifuged at 10K×g to remove microvesicles and the supernatant used for exosome analysis. As a control, 100K×g centrifugation was carried out for 2 hours and the pellet used directly for protein extraction with no washing step. The supernatant from the 100K UC sample was then captured on EVTRAP beads to analyze the exosomes left after the ultracentrifugation step. For the sample comparison, 10K supernatant and 1 mL of concentrated urine were also captured by EVTRAP. We have previously developed a highly effective protocol for EV protein extraction using phase-transfer surfactant and applied it for plasma EV analysis. In this project, we used this protocol for EV lysis and extraction, followed by on-beads digestion and LC-MS analysis. While we used 1 mL of the 10× concentrated urine as the starting material, only 2% of each sample was loaded onto the LC column for LC-MS analysis (equivalent to only 200 µL of starting urine amount). Using a single 90-min LC-MS gradient, we were able to identify >16,000 unique peptides from ~2,000 unique proteins from the EVTRAP experiment. By comparison, 100K UC method produced >7,200 unique peptides from ~1,100 unique proteins. EVTRAP capture of the 100K supernatant again showed that the majority of the exosomes were not recovered by the ultracentrifugation, but could then be captured by EVTRAP.

Label-free quantitation was utilized to compare all of the proteins identified by each method. ExoCarta is a web-based exosome data compendium and a useful tool that collects a large number of EV studies. They produced a list of 100 top exosome markers and exosome-enriched proteins that were found by most published studies. In our experiment, we have identified 94 of these exosome proteins (including common markers like CD9, CD63, CD81, TSG101), with all of them showing a significant increase after EVTRAP capture. This is significant because many other studies have shown that different methods are able to enrich different exosome populations with various success rates. In EVTRAP, it appears that the complete EV profile is recovered. As an example of the data, we have listed a few common exosome markers in a bar chart in FIG. 4A. The average fold increase of all detected exosome markers compared to the 100K UC sample is shown in FIG. 4B. When using the 10K supernatant (exosomes only fraction) for EVTRAP experiment (EV3 data point), the average increase in marker signal is ~9-fold, which matches very well with the Western Blot data. However, when the complete urine is used without MV removal (EV4 data point), the increase over the control is almost 17-fold.

As has been previously suggested for minimal EV study requirements, we wanted to make sure the contamination levels of free urine proteins identified are reasonable. We found 42 common urinary proteins in our data not known to associate with EVs (including the ubiquitous uromodulin), and listed 5 of them in the same bar chart (FIG. 4A). The average increase in contaminant level for all 42 proteins is also provided in FIG. 4B. As can be seen, the contamination levels follow very closely to the marker quantitation levels, demonstrating similar ratio of exosome markers to the contaminating proteins as in the UC sample. We expect that the contamination levels can be further reduced by detergent-based washing steps of EVTRAP beads.

Example 4

Figure 5A:
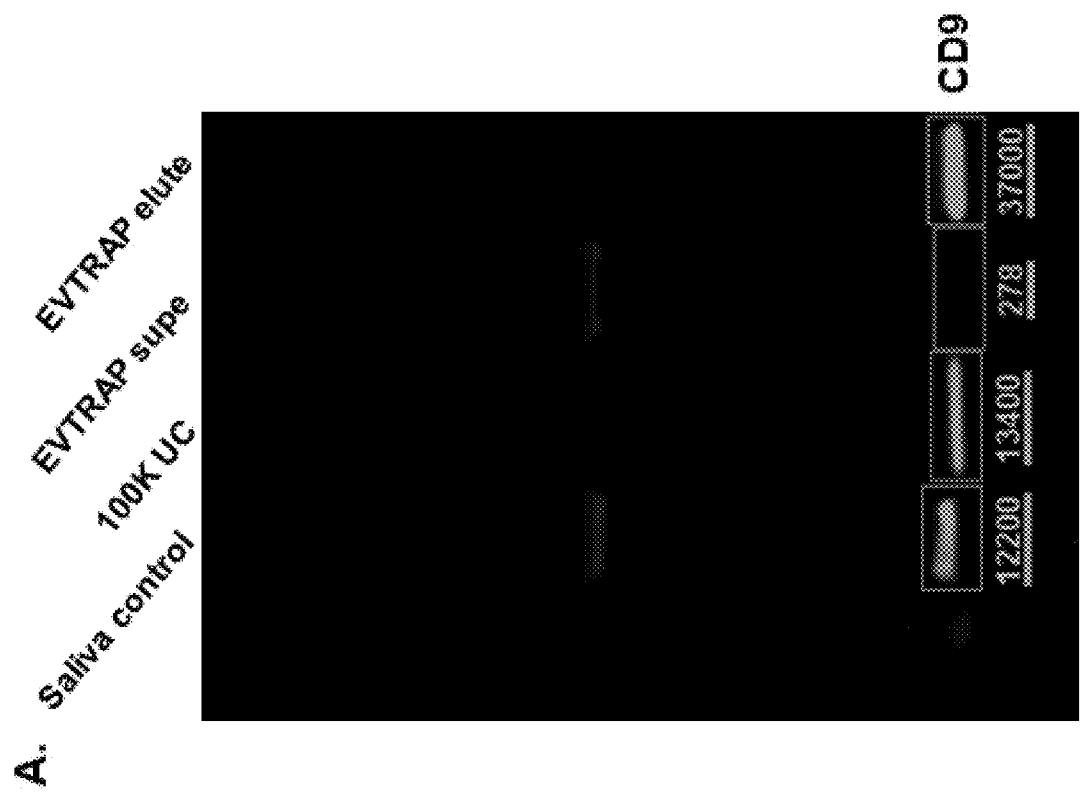
FIG. 5A displays a saliva comparison between UC and EVTRAP for exosome capture via detection of CD9 exosome marker using Western Blot.
Figure 5B:
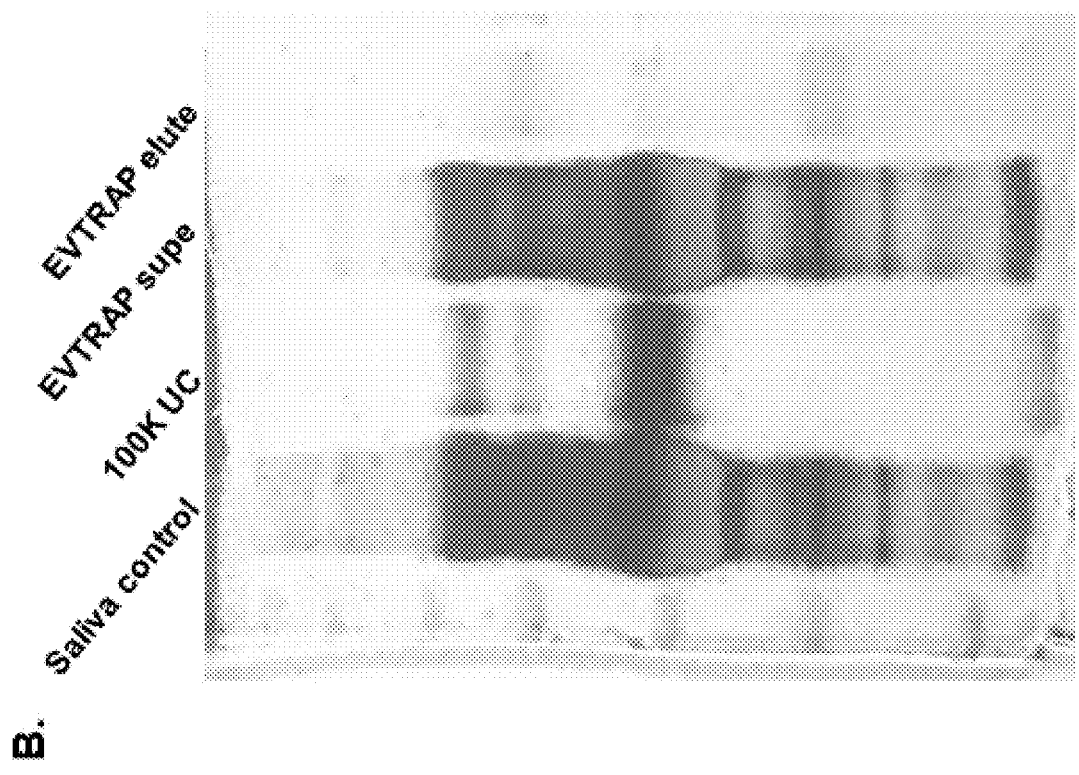
FIG. 5B displays a saliva comparison between UC and EVTRAP for exosome capture via silver stain total protein detection of global EV population capture from saliva.
Figure 6A:
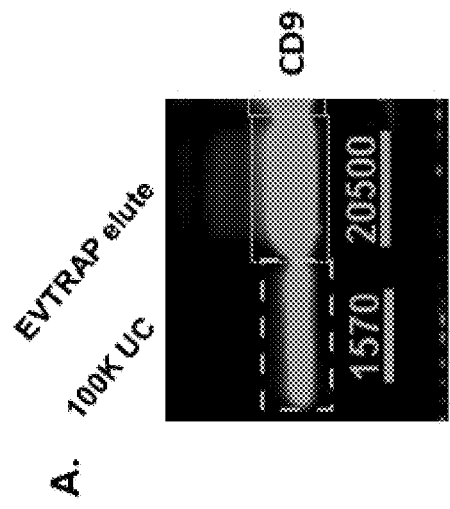
FIG. 6A displays plasma comparison between Ultracentrifugation (UC), 10K centrifugation and EVTRAP for EV capture via detection of CD9 exosome marker.
Figure 6B:
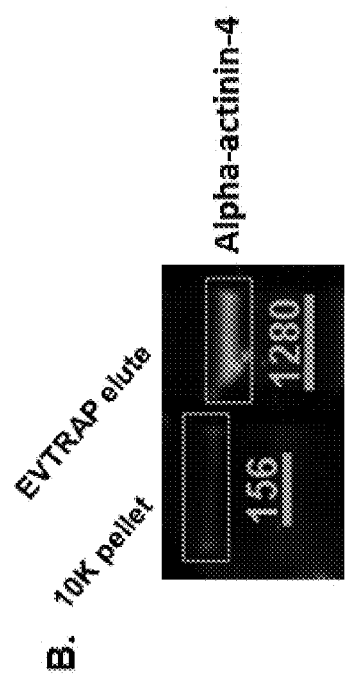
FIG. 6B displays plasma comparison between Ultracentrifugation (UC), 10K centrifugation and EVTRAP for EV capture via alpha-actinin-4 microvesicles marker using Western Blot.

A saliva sample is analyzed via two different methods to capture and purify extracellular vesicles, ultracentrifugation and EVTRAP. Then the exosome is analyzed with western blot.
EV Capture from Saliva and Plasma While all the previous experiments for EVTRAP capture were carried out in urine, we made sure the EV capture and isolation also works well in other sample types. We carried out comparison experiments between 100K ultracentrifugation and EVTRAP using saliva or plasma as the source (FIG. 5 is for saliva; FIG. 6 is for plasma) similar to Example 1. In the saliva experiment, EVTRAP again showed a significant improvement in exosome capture compared to UC (CD9 exosome marker signal in FIG. 5A), with no to minimal amount of exosomes remaining in EVTRAP supernatant. Silver stain total protein detection of the sample samples showed that EVTRAP also produced cleaner EV population than UC with much less contaminating proteins (FIG. 5B).

Example 5

A plasma sample is analyzed via two different methods to capture and purify extracellular vesicles, ultracentrifugation and EVTRAP. Then the exosome is analyzed and the CD9 marker is detected with western blot.

Similarly, for plasma samples we carried out comparison experiments between 100K ultracentrifugation, 10K centrifugation to pellet microvesicles, and EVTRAP. As results in FIG. 6 demonstrate, EVTRAP resulted in >10-fold increase in exosome signal (CD9 exosome marker WB in FIG. 6A) and 8-fold increase in microvesicles signal (alpha-actinin-4 microvesicles marker WV in FIG. 6B).

Example 6

Figure 7A:
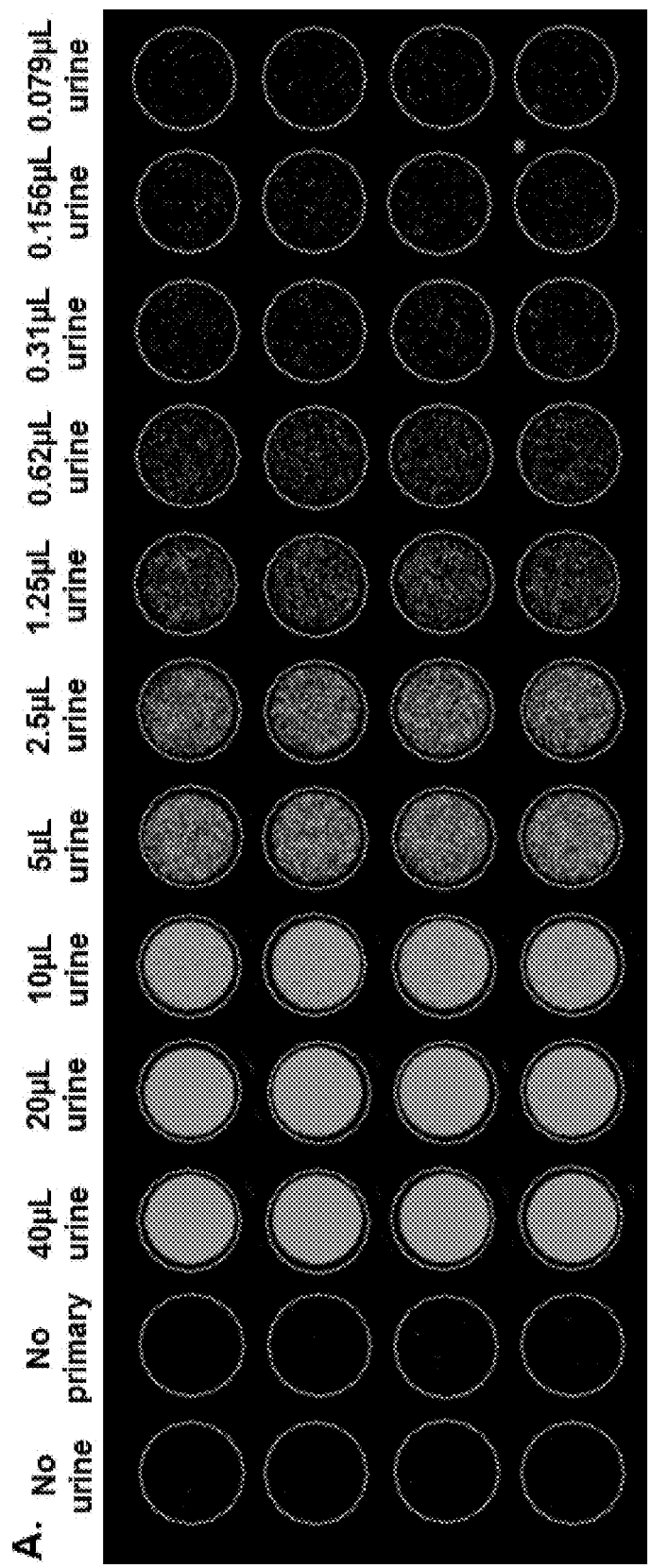
FIG. 7A displays EVTRAP capture of urine EVs and on-beads detection using anti-CD9 antibody.
Figure 7B:
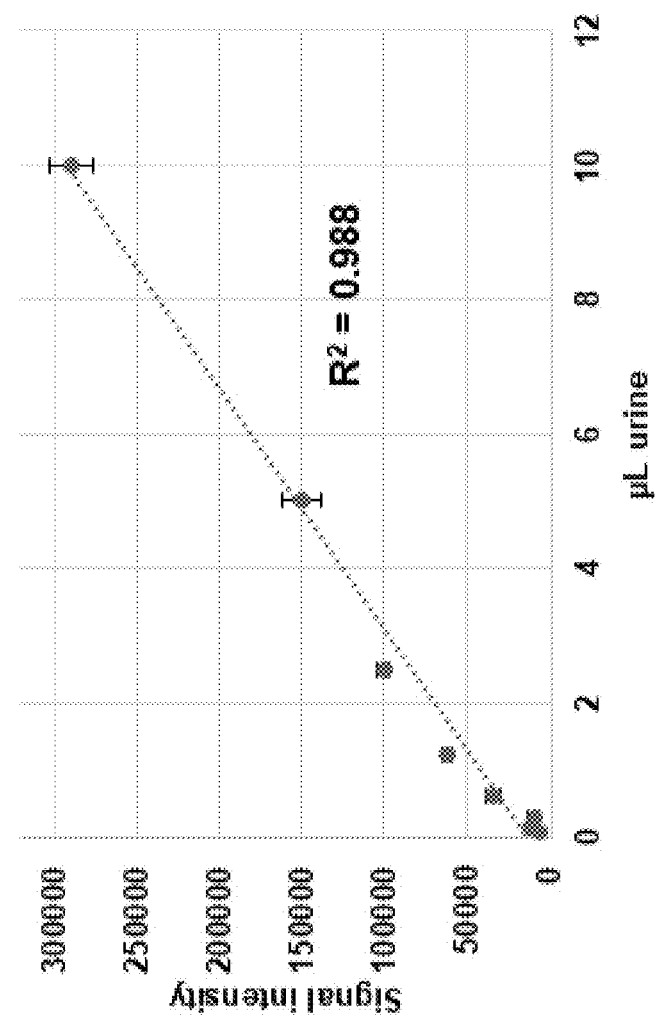
FIG. 7B displays quantitation of the signal in FIG. 7A from 0.079 µL to 10 µL of urine.

The signal response of the EVTRAP method at varied sample concentrations is evaluated.
On-Beads Detection of Captured EVs Majority of the EV data we and others have generated focus on analysis of the internal cargo (RNA, DNA, proteins, phosphoproteins). However, in some cases detection and quantitation of exosome surface proteins is sufficient. To demonstrate this capability, we captured various increasing amounts of 10× concentrated urine onto the same volume of EVTRAP beads. We then detected the fluorescent signal after incubation of the beads with anti-CD9 primary and fluorophore-labeled secondary antibodies. We can see from FIG. 7A that the captured exosomes can be easily detected directly on beads from as little as 0.1 µL concentrated urine (corresponding to 1 µL original urine). The capture and detection are also highly quantitative for up to 10 µL of concentrated urine (where the experiment reached the upper limit of in-well detection; FIG. 7B). The negative control wells where no urine or no primary antibody were added produced no detectable signal.

Example 7

Cell culture media was collected, and any remaining cells and apoptotic bodies removed. The EVs (exosomes) from 0.5 mL of the cell culture media were then captured by the magnetic EVTRAP beads using end-over-end rotation for 1 hour. The beads were separated from the solution by magnetic separator rack, and the solution discarded. The beads were washed twice by PBS, and the bound EVs were eluted by incubation with 100 mM triethylamine for 10 minutes. The eluted sample was dried, the EVs lysed with LDS sample loading buffer and loaded on the gel.

As a control, the EVs were isolated using the standard procedure of differential centrifugation. Briefly, the cell culture media was centrifuged for 1 hour at 10,000×g (10K pellet) and the supernatant collected. Then, the 10K supernatant was centrifuged again using an ultracentrifuge at 100,000×g (100K pellet). The EV pellets were lysed with LDS sample loading buffer and loaded on the gel.

Figure 8A:
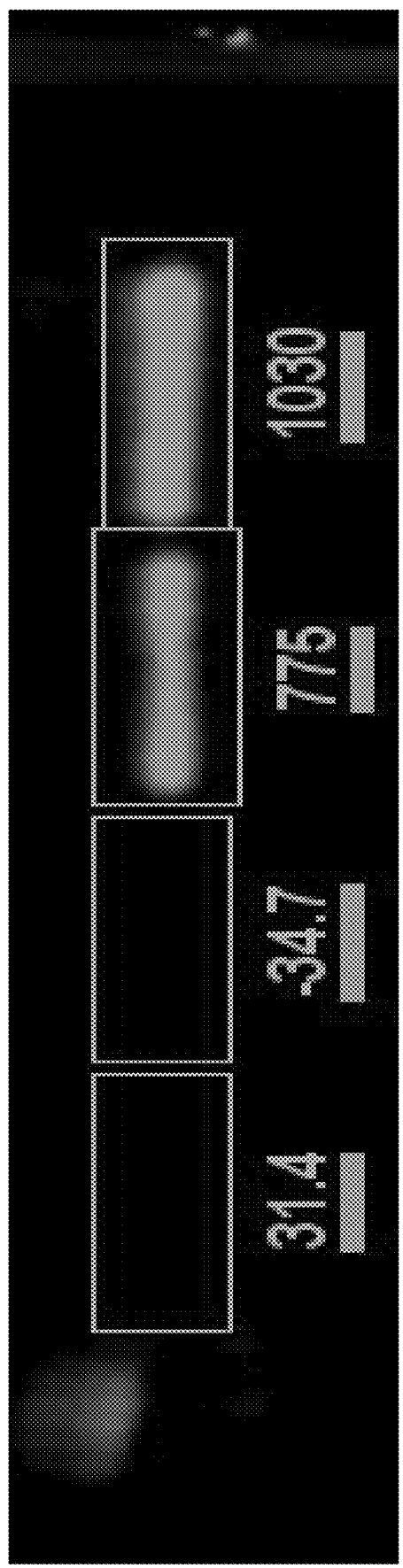
FIG. 8A displays comparison between UC and EVTRAP for exosome capture via detection by exosome marker CD9 using Western Blot from cell culture media. Lane 1 contains 10K UC pellet, lane 2 contains 100K UC pellet, lane 3 contains EVTRAP of 100K UC supernatant, and lane 4 contains EVTRAP from cell culture media.
Figure 8B:
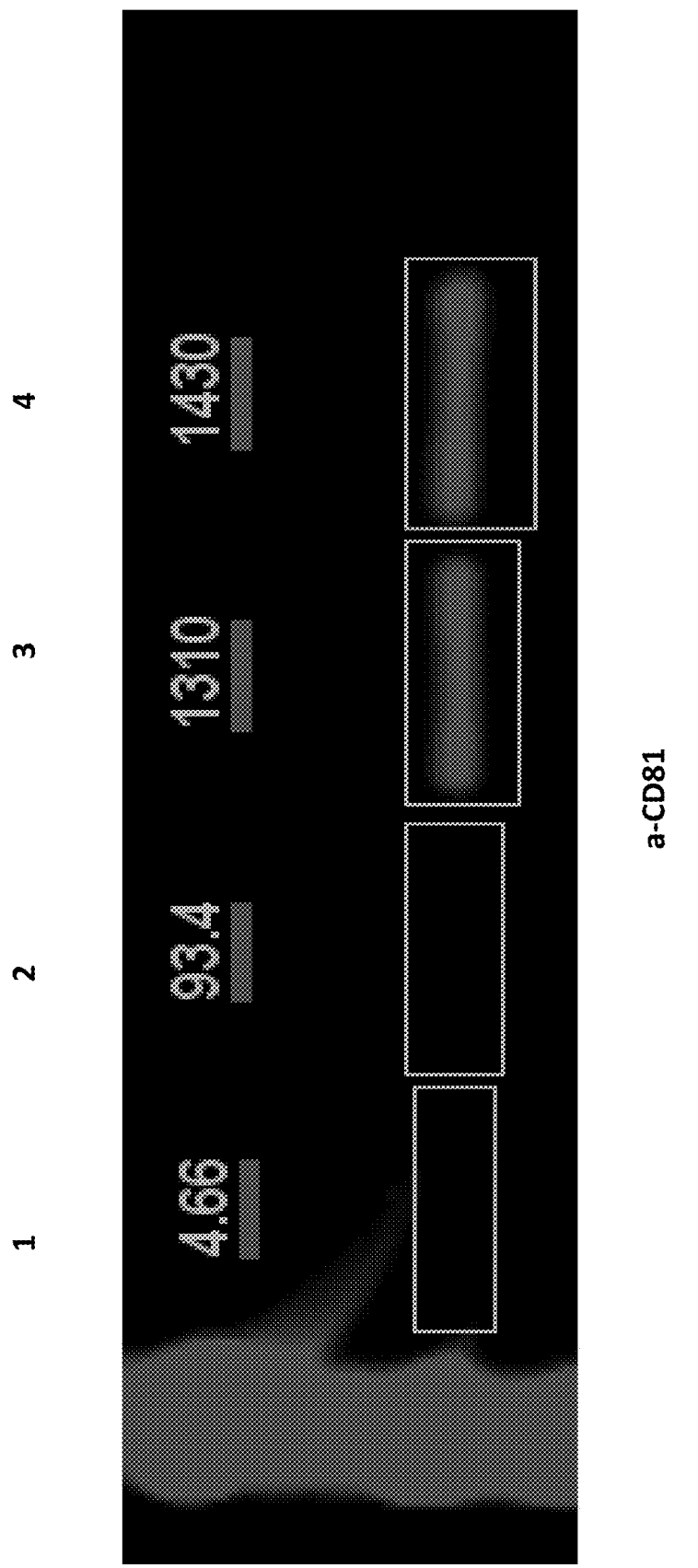
FIG. 8B displays comparison between UC and EVTRAP for exosome capture via detection by exosome marker CD81 using Western Blot from cell culture media. Lane 1 contains 10K UC pellet, lane 2 contains 100K UC pellet, lane 3 contains EVTRAP of 100K UC supernatant, and lane 4 contains EVTRAP from cell culture media.

As illustrated by lane 3 of FIGS. 8A and 8B, the supernatant from the 100K UC sample was then captured on EVTRAP beads to analyze the exosomes left after the ultracentrifugation step.

After running the gel, the proteins were transferred to a PVDF membrane, the membrane blocked and immunoblotted against anti-CD9 or anti-CD81 proteins (both are markers for exosomes). The resulting signal was detected using secondary anti-rabbit antibodies labeled with 800 nm Dye (for CD9; See FIG. 8A), or 680 nm Dye (for CD81; See FIG. 8B).

In both 10K and 100K pellets, not much CD9 or CD81 signal was observed, demonstrating that very few exosomes are being captured by the differential centrifugation approach. EVTRAP is able to catch a significantly higher amount. The EVs remaining after ultracentrifugation in the supernatant can still be captured by EVTRAP.

Example 8

Similar to Example 7, cell culture media was collected, and any remaining cells and apoptotic bodies removed. Differences to Example 7 will be disclosed. The Evs (exosomes) from 10 mL of the cell culture media were than captured by the magnetic EVTRAP beads using end-over-end rotation for 1 hour.

As a control and as similar to Example 7, the EVs were isolated using the standard procedure of differential centrifugation. Briefly, the cell culture media was centrifuged for 1 hour at 10,000×g (10K pellet) and the supernatant collected. Then, the 10K supernatant was centrifuged again using an ultracentrifuge at 100,000×g (100K pellet).

The EVTRAP and 100K pellet samples were lysed by phase-transfer aided surfactant solution and digested using Lys-C and trypsin. The resulting peptides were desalted by C18 Sep-Pak columns. 1% of each sample was taken out and analyzed by mass spectrometry directly to obtain proteomics data. The remaining 99% were used for PolyMAC-based enrichment of phosphopeptides, and the resulting phosphopeptides were analyzed by the mass spectrometry.

Figures 9A, 9B:
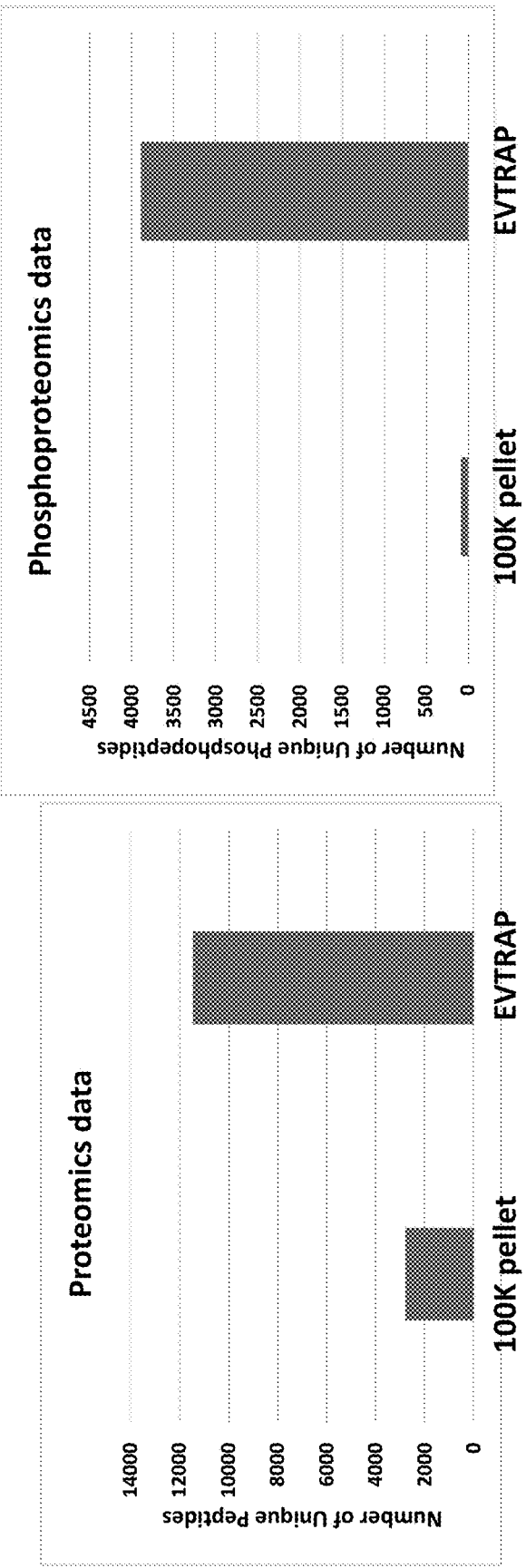
FIG. 9A displays LC-MS total proteome analysis of 100K UC and EVTRAP samples from cell culture media.
FIG. 9B displays LC-MS phosphoproteome analysis of 100K UC and EVTRAP samples from cell culture media.

As best illustrated in FIG. 9A, the EVTRAP exosome capture approach of Example 8 identified 4 times more unique peptides than 100K ultracentrifugation procedure. As best illustrated in FIG. 9B, the EVTRAP exosome capture approach of Example 8 identified 47 times more unique phosphopeptides than 100K ultracentrifugation procedure.

Example 9

The EVs from 0.05 mL of the previously collected patient cerebrospinal fluid (CSF) were captured by the magnetic EVTRAP beads using end-over-end rotation for 1 hour. The rest of the procedure is the same as in Example 7.

After running the gel, the proteins were transferred to a PVDF membrane, the membrane blocked and immunoblotted against a common marker for exosomes, anti-CD9 protein. The resulting signal was detected using secondary anti-rabbit antibody labeled with 800 nm Dye.

Figure 10:
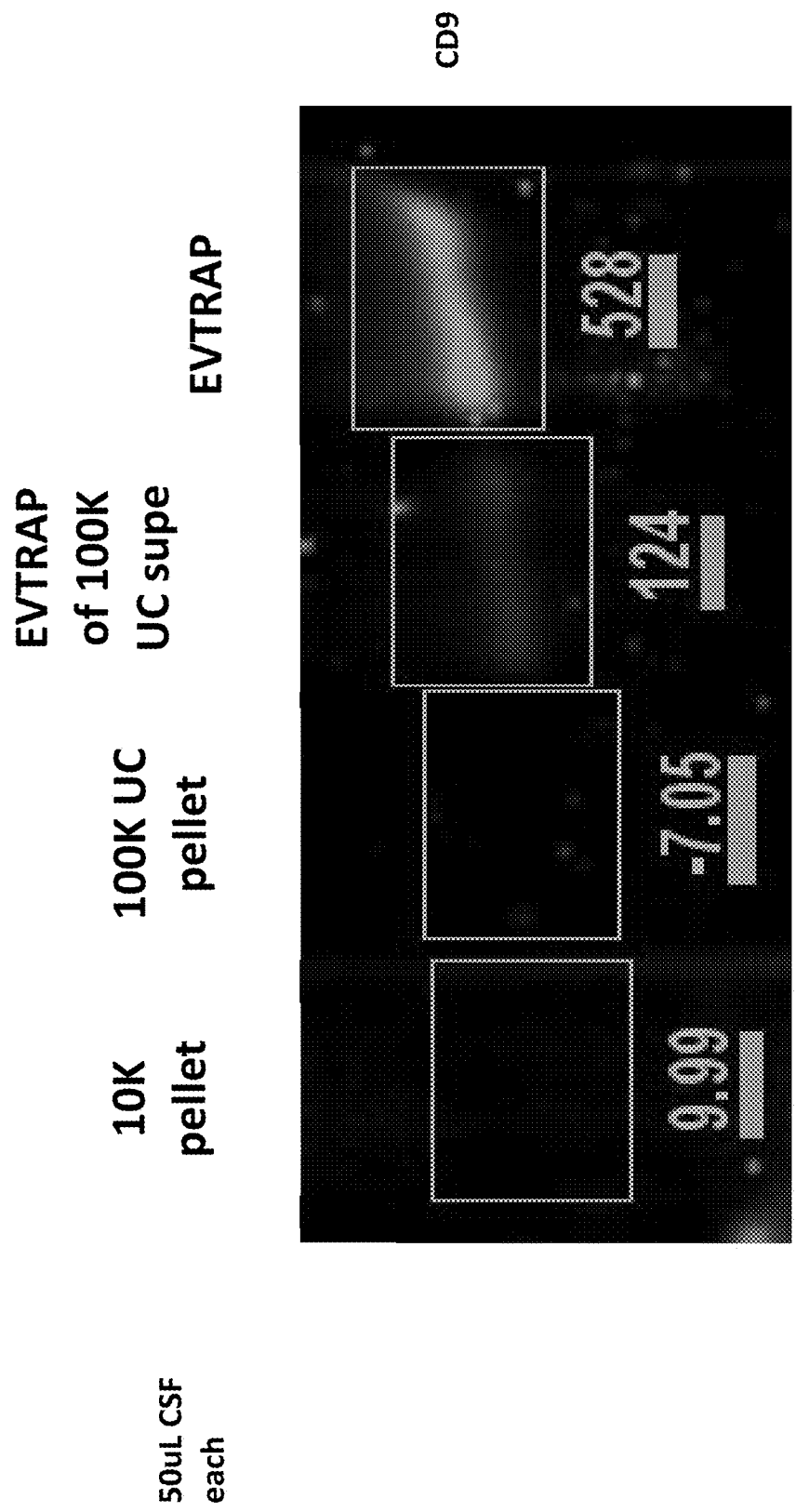
FIG. 10 displays comparison between UC and EVTRAP for exosome capture via detection by exosome marker CD9 using Western Blot from cerebral spinal fluid.

As best illustrated in FIG. 10, in both 10K and 100K pellets, not much CD9 signal was observed, demonstrating that very few exosomes are being captured by the differential centrifugation approach. EVTRAP is able to catch a significantly higher amount. The EVs remaining after ultracentrifugation in the supernatant can still be captured by EVTRAP.

Example 10

The Evs (exosomes) from 1 mL of the previously collected patient cerebrospinal fluid (CSF) were captured by the magnetic EVtrap beads using end-over-end rotation for 1 hour. The rest of the procedure is the same as in Example 8 with the following exceptions. 10% of each sample was taken out and analyzed by mass spectrometry directly to obtain proteomics data, instead of 1%. The remaining 90% were used for PolyMAC-based enrichment of phosphopeptides, and the resulting phosphopeptides were analyzed by the mass spectrometry.

Figure 11A:
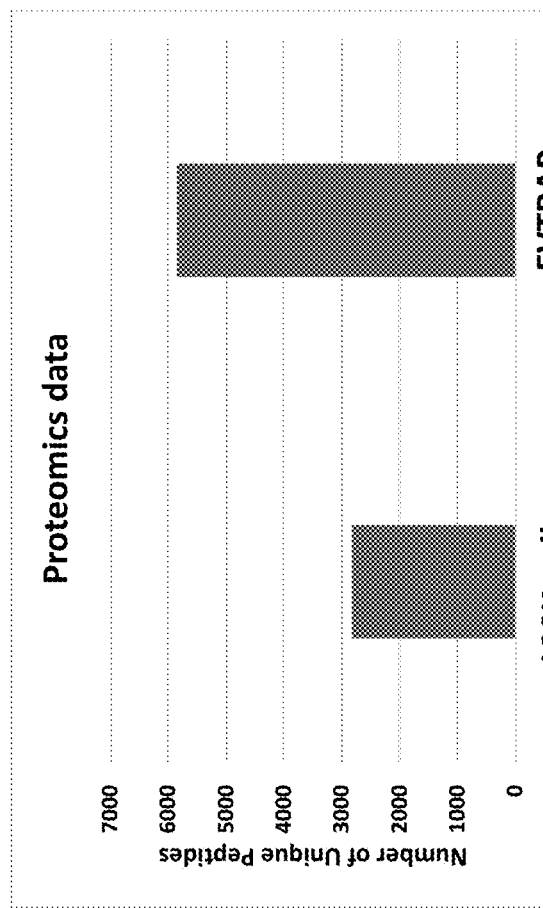
FIG. 11A displays LC-MS total proteome analysis of 100K UC and EVTRAP samples from cerebral spinal fluid.
Figure 11B:
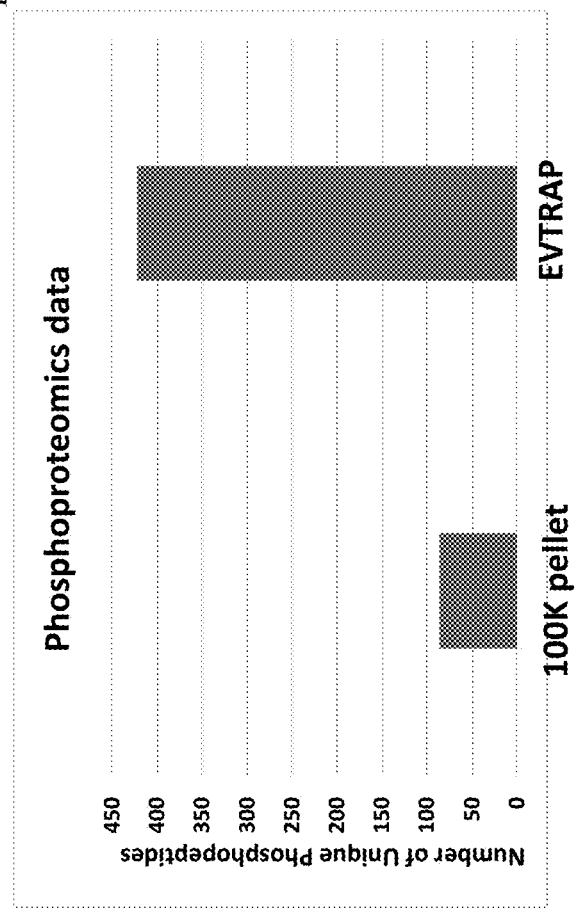
FIG. 11B displays LC-MS phosphoproteome analysis of 100K UC and EVTRAP samples from cerebral spinal fluid.

As best illustrated in FIG. 11A, EVTRAP exosome capture approach of Example 10 identified 2 times more unique peptides than 100K ultracentrifugation procedure. As best illustrated in FIG. 11B, EVTRAP exosome capture approach of Example 10 identified 6 times more unique phosphopeptides than 100K ultracentrifugation procedure.

While this disclosure has been described as having an exemplary design, the present disclosure may be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains.

What is claimed is:

1. A method to selectively capture and purify extracellular vesicles from biofluids using lipid affinity-based capture, the method comprising:
   providing a biofluid;
   providing a surface, wherein the surface is coated with a combination of at least one hydrophilic group and at least one hydrophobic group, wherein the at least one hydrophilic group and at least one hydrophobic group are coated directly onto the surface, to render a modified surface;
   mixing the modified surface with the biofluid;
   selectively and reversibly binding native extracellular vesicles (EV) from the biofluid directly to the modified surface, wherein the at least one hydrophilic group or the at least one hydrophobic groups bind only to the surface of the EV;
   isolating the modified surface containing the selectively and reversibly bound EV; and
   extracting the bound EV from the modified surface containing the selectively and reversibly bound EV.

2. The method of claim 1, wherein the hydrophilic group is a polyethylene oxide.

3. The method of claim 1, wherein the hydrophobic group is a phenyl ether.

4. The method of claim 1, wherein the modified surface includes a dendrimer.

5. The method of claim 4, wherein the dendrimer further comprises titanium ions.

6. The method of claim 1, wherein the biofluid is urine.

7. The method of claim 1, wherein surfactants are added to the biofluid.

8. The method of claim 1, further comprising the step of extracting at least one internal EV content.

9. The method of claim 8, wherein the step of extracting is performed using solutions of 2-[4-(2,4,4-trimethylpentan-2-yl)phenoxy]ethanol 2-[4-(2,4,4-trimethylpentan-2-yl)phenoxy]ethanol.

10. The method of claim 8, wherein the at least one internal EV content include proteins, post-translationally modified proteins, DNA, mRNA, miRNA, metabolites, and gene mutations.

11. The method of claim 8, further comprising the step of analyzing the EV contents.

12. The method of claim 11, wherein the step of analyzing is performed using mass spectrometry.

13. The method of claim 1, wherein the step of extracting the bound EV from the modified surface containing the selectively and reversibly bound EV is performed using a triethylamine elution to obtain intact EV.

14. The method of claim 1, further comprising the step of detecting EV from the modified surface containing the selectively bound EV.

15. The method of claim 14, wherein the step of detecting is performed using antibodies.

16. The method of claim 15, further comprising the step of characterizing the EV from the modified surface containing the selectively bound EV.

17. The method of claim 1, further comprising removing cells and large apoptotic bodies from the biofluid with centrifugation.

18. The method of claim 1, wherein the extracting step achieves at least 90% EV recovery from the biofluid.

19. The method of claim 1, wherein the at least one hydrophilic group and the at least one and hydrophobic group are both non-ionic.

20. A method to selectively capture and purify extracellular vesicles from biofluids using lipid affinity-based capture, the method comprising:
   providing a biofluid;
   providing a surface, wherein the surface is coated with a combination of at least one hydrophilic group and at least one hydrophobic group, wherein the at least one hydrophilic group at least one hydrophobic group are coated directly onto the surface, to render a modified surface;
   mixing the modified surface with the biofluid;
   selectively and reversibly binding native extracellular vesicles (EV) from the biofluid directly to the modified surface, wherein the at least one hydrophilic group or the at least one hydrophobic groups bind only to the surface of the EV;
   isolating the modified surface containing the selectively and reversibly bound EV; and
   extracting the bound EV from the modified surface containing the selectively and reversibly bound EV.

* * * * *